(12) United States Patent  
Allendorf et al.

(10) Patent No.: US 8,065,904 B1  
(45) Date of Patent: Nov. 29, 2011

(54) METHOD AND APPARATUS FOR DETECTING AN ANALYTE

(75) Inventors: Mark D. Allendorf, Pleasanton, CA (US); Peter J. Hesketh, Atlanta, GA (US)

(73) Assignee: Sandia Corporation, Livermore, CA (US)

( * ) Notice: Subject to any disclaimer, the term of this patent is extended or adjusted under 35 U.S.C. 154(b) by 737 days.

(21) Appl. No.: 12/137,635

(22) Filed: Jun. 12, 2008

Related U.S. Application Data

(60) Provisional application No. 60/936,283, filed on Jun. 18, 2007.

(51) Int. Cl.
 *G01N 27/00* (2006.01)
 *G01N 33/497* (2006.01)

(52) U.S. Cl. .................................. 73/31.06; 73/23.2

(58) Field of Classification Search ............. 73/23.21, 73/23.34, 24.01, 24.04, 24.06, 29.01, 29.02, 73/335.05, 335.11, 29.05, 31.01–31.03, 31.05, 73/31.06

See application file for complete search history.

(56) References Cited

U.S. PATENT DOCUMENTS

| | | | |
|---|---|---|---|
| 5,445,008 A | 8/1995 | Wachter | |
| 5,918,263 A | 6/1999 | Thundat | |
| 6,420,706 B1 | 7/2002 | Lurie | |
| 6,797,631 B2 | 9/2004 | Kim | |
| 6,864,692 B1* | 3/2005 | Patel et al. | 324/661 |
| 6,935,165 B2 | 8/2005 | Bashir | |
| 6,977,511 B2* | 12/2005 | Patel et al. | 324/661 |
| 7,141,385 B2 | 11/2006 | Bottomley | |
| 7,168,298 B1* | 1/2007 | Manginell et al. | 73/54.25 |
| 7,207,206 B2 | 4/2007 | Pinnaduwage | |
| 7,340,941 B1 | 3/2008 | Fruhberger | |
| 2004/0007051 A1 | 1/2004 | Bashir | |
| 2005/0262943 A1* | 12/2005 | Claydon et al. | 73/579 |
| 2007/0202038 A1* | 8/2007 | Yaghi et al. | 423/702 |
| 2009/0203000 A1* | 8/2009 | Mutharasan et al. | 73/24.06 |
| 2010/0132549 A1* | 6/2010 | Yaghi et al. | 95/128 |

OTHER PUBLICATIONS

Warrensford, Daniel E. "Gas-solid absorption characteristics of supramolecular compounds using a hermetically controlled atmosphere automated absorption balance (H-CAAAB)." Air Force Inst of Tech Wright-PattersonAFB OH. Nov. 18, 2002. Accessed online on Mar. 14, 2011 at <http://handle.dtic.mil/100.2/ADA410639>.*

R. Shediac, E. Lai, C. Bauer, B. Simmons, R. Stumpf, A. Choudhury, P. Hesketh, M. Allendorf, "Growth of Metal Organic Frameworks onto Microcantilever Substrate Materials", Meet. Abstr.—Electrochem. Soc. 602, 1757 (Oct. 29-Nov. 3, 2006).*

S. Hermes, D. Zacher, A. Baunemann, C. Woll, R. A. Fischer, "Selective growth and MOCVD loading of small single scrystals of MOF-5 at alumina and silica surfaces modified with organic self-assembled monolayers" Chem. Mater. 19, pp. 2168-2173 (Apr. 7, 2007).*

Q. Yang and C. Zhong, "Molecular simulation of carbon dioxide/methane/hydrogen mixture adsorption in metal-organic frameworks" J. Phys. Chem B, (Aug. 19, 2006), 110, pp. 17776-17783.*

(Continued)

*Primary Examiner* — Lisa Caputo  
*Assistant Examiner* — Punam Roy  
(74) *Attorney, Agent, or Firm* — Timothy Evans

(57) ABSTRACT

We describe the use of coordination polymers (CP) as coatings on microcantilevers for the detection of chemical analytes. CP exhibit changes in unit cell parameters upon adsorption of analytes, which will induce a stress in a static microcantilever upon which a CP layer is deposited. We also describe fabrication methods for depositing CP layers on surfaces.

24 Claims, 7 Drawing Sheets

OTHER PUBLICATIONS

F. M. Battiston; J.-P. Ramseyer; H. P. Lang; M. K. Baller; CH. Gerber; J. K. Gimzewski; E. Meyer; H.-J. Guntherodt; "A chemical sensor based on a microfabricated cantilever array with simultaneous resonance-frequency and bending readout", Sensors and Actuators B, 2001, vol. 77, pp. 122-131.

Q. M. Wang; D. Shen; M. Bulow; M. L. Lau; S. Deng; F. R. Fitch; N. O. Lemcoff; J. Semanscin; "Metalloorganic molecular sieve for gas separation and purification", Microporous and Mesoporous Materials, 2002, vol. 55, pp. 217-230.

J. Zhou; P. Li; S. Zhang; Y. Huang; P. Yang; M. Bao; G. Ruan; "Self-excited piezoelectric microcantilever for gas detection", Microelectronic Engineering, 2003, vol. 69, pp. 37-46.

J. Zhou; P. Li; S. Zhang; Y. Long; F. Zhou; Y. Huang; P. Yang; M. Bao; "Zeolite-modified microcantilever gas sensor for indoor air quality control", Sensors and Actuators B, 2003, vol. 94, pp. 337-342.

R. Matsuda; R. Kitaura; S. Kitagawa; Y. Kubota; T. C. Kobayashi; S. Horike; M. Takata; "Guest Shape-Responsive Fitting of Porous Coordination Polymer with Shrinkable Framework", Journal of American Chemical Society, 2004, vol. 126, pp. 14063-14070.

K. Uemura; R. Matsuda; S. Kitagawa; "Flexible microporous coordination polymers", Journal of Solid State Chemistry, 2005, vol. 178, pp. 2420-2429.

S. Hermes; D. Zacher; A. Baunemann; C. Woll; R. A. Fisher; "Selective Growth, and MOCVD Loading of Small Single Crystals of MOF-5 at Alumina and Silica Surfaces Modified with Organic Self-Assembled Monolayers", Chemical Materials, 2007, vol. 19, pp. 2168-2173.

S. Singamaneni, M. E. McConney; M. C. Lemieux; H. Jiang; J. O. Enlow; T. J. Bunning; R. R. Naik; V. V. Tsukruk; "Polymer-Silicon Flexible Structures for Fast Chemical Vapor Detection", Advanced Materials, 2007, vol. 19, pp. 4248-4255.

K. M. Goeders; J. S. Colton; L. A. Bottomley; "Microcantilevers: Sensing Chemical Interactions via Mechanical Motion", Chemical Review, 2008, vol. 108, pp. 522-542.

\* cited by examiner

METHOD AND APPARATUS FOR DETECTING AN ANALYTE

CROSS REFERENCE TO RELATED APPLICATIONS

This application claims priority to prior co-pending provisional U.S. Patent Application Ser. No. 60/936,283 originally filed Jun. 18, 2007 entitled "METHOD AND APPARATUS FOR DETECTING AN ANALYTE" from which benefit is claimed.

STATEMENT OF GOVERNMENT SUPPORT

The United States Government has a paid-up license in this invention and the to right in limited circumstances to require the patent owner to license others on reasonable terms as provided for by the terms of contract No. DE-AC04-94AL85000 awarded by the U.S. Department of Energy to Sandia Corporation.

BACKGROUND OF THE INVENTION

The present invention relates generally to a sensor for detecting molecular species at very low concentrations. More specifically, the present invention relates to a microcantilever which is coated with a porous material capable of absorbing various molecular species either from the surrounding air or from a liquid solution.

PRIOR ART

Coordination polymers (CP), such as carboxylates, are a class of hybrid inorganic-organic, crystalline materials whose structure and properties can be rationally tailored by the selection of their component chemical moieties. Distinguishing features of a CP are coordinating metallic groups causing organic ligands to self-organize into two- or three-dimensional open-pore structures. These structures retain their porosity upon removal of "guest" molecules (e.g., a solvent or other similar molecule), enabling them to serve as reversible sorbents for a variety of molecular species. Examples of CPs reported in the literature include the series of CP structures known as iso-reticular (IR) metal organic frameworks (MOF) of zinc-carboxylate; and the so-called MIL-series of iron- and chromium-carboxylate (MOF) compounds (MIL stands for "Materials of Institut Lavoisier," a research center associated with Versailles Saint-Quentin-en-Yvelines University, France), zeolite imidazolate frameworks, and covalent organic frameworks (COF), in which the crystalline nanoporous structure comprises a network of inorganic atoms (typically silicon and/or boron) covalently bonded to organic linking groups.

Importantly, CP crystal structures exhibit a high degree of structural flexibility not found in other nanoporous materials, such as zeolites, aerogels, synthetic opals, and nanotubes (both carbon- and non-carbon based). When CP materials absorb molecules from either a gas or solution phase, many undergo reversible changes in the size and/or shape of their individual unit cell structure. The nature of these changes can take several forms. Uemura et al., ("Flexible macroporous coordination polymers," *Journal of Solid State Chemistry*, 2005, v. 178(8): pp. 2420-2429) reviewed these effects and divided CP pores into four categories, comprising: i) induced fit; ii) breathing; iii) guest-exchange deformation; and iv) healing-type pores. Both pore shrinkage and expansion are observed. In some cases, only the unit cell dimensions change. In other cases, the space group of the lattice changes as well. Crystalline to amorphous transformations are also observed. The magnitude of these changes varies from quite small (<1% of the unit-cell volume for IRMOF-1 upon adsorption of the solvent dimethylformamide; DMF) to extremely large (230%) in the case of the dried vs. hydrated forms of MIL-88D.

These structural changes suggest a route for detecting molecular species by sensing the stress induced into the coating structure at the interface between a flexible CP layer and a static microcantilever, using either a built-in piezoresistive stress sensor or by measuring (optically or otherwise) the induced bending that occurs as the molecular species is absorbed into the CP layer.

Static microcantilevers detect the presence of adsorbed molecules by sensing changes in surface energy caused by the adsorption of the molecules. Examples include U.S. Pat. Nos. 5,918,263 to Thundat; 6,935,165 to Bashir, et al.; 7,207,206 to Pinnaduwage, et al.; and 7,340,941 to Fruhberger, et al.; and published U.S. Patent Application Serial Number 20040007051 to Bashir, et al. Such changes can be caused by the mere adsorption on the surface (for example, adsorption of a thiolate onto a gold-coating fixed to a surface of a microcantilever) or by the swelling of an amorphous material such as a polymer. However, changes caused by the lattice mismatch between the crystal structures of dissimilar materials can be particularly large. For example, thin films deposited on substrates by vapor deposition methods (e.g., chemical or physical vapor deposition) can, in some instances, generate enough stress within the film that the film cracks and detaches from the substrate. The magnitude and nature (tensile or compressive) of these stresses depends on the mechanical properties (specifically, the Young's modulus) and the relative size of the unit cells of the substrate and coating materials which are used.

SUMMARY

CP coatings on microcantilevers possess a number of features that make them potentially far superior to polymer coatings currently being used. In particular, large stress-induced signals are expected to be induced upon adsorption due to the large changes in lattice dimensions that can be achieved. Moreover, some CP materials possess surface areas of up to 6,000 $m^2$/g, which is nearly six times greater than the highest surface areas observed in a zeolite, making them potentially highly effective sorbants. In addition, by changing the chemical nature of the linking molecule, the metal center, and/or the pore geometry, it is possible to tailor the size and shape of the pores of these materials, which in turn enables the practitioner to specify both the chemical selectivity and adsorption properties of these materials in a rational manner. Finally, an effective mechanical linkage between CP crystals and a substrate can be created by covalent bonding schemes that anchor the crystal to the cantilever surface.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF EMBODIMENTS OF THE INVENTION

In the following detailed description, reference is made to the accompanying drawings which form a part hereof and in which is shown, by way of illustration, specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope of the present invention is defined by the appended claims.

Various methods can be used for measuring surface stress using CP coatings such as metal organic framework (MOF) materials, zeolite imidazolate framework materials, and any other crystalline material comprised of organic and/or inorganic portions and having a porous structure. These methods include growing surface coatings on a piezoelectric substrate such as aluminum nitride (AlN); growing surface coatings on a capacitive sensor membrane, or growing surface coatings on a membrane that is part of an Extrinsic Fabry-Perot Interferometer (EFPI) strain sensor. Moreover, besides static strain sensing, the change in the mass of the CP coating as a result of analyte absorption is also detectable as a frequency shift in the case of a vibrating beam, or any other resonant structure, e.g., a tuning fork. Furthermore, it is likely that both cantilever bending and frequency shift could be detected with a single element.

The preferred embodiment of the present invention, however, comprises a simple microcantilever assembly having a piezoresistive stress sensor fixed thereto and a flexible CP layer deposited on one or both surfaces of the microcantilever assembly. Depending upon the application, CP layers are chosen for their compatibility with their environment. For instance, if the sensor was to be used to detect trace material in a liquid media, the CP layer is selected from materials which are stable in the media, or if the sensor is deployed in a gaseous atmosphere, the CP layer is selected from materials that do not react irreversibly with the gas or gases of the target atmosphere. For example, zinc-carboxylate metal organic frameworks (MOF) such as IRMOF-1 may be appropriate for detection of gases in dry atmospheres, while the nickel MOF $Ni_2(4,4'\text{-bipyridine})_3(NO_3)_4$ could be used for detecting analytes in organic solvents. Alternatively, a water-stable MOF such as HKUST-1 ($[Cu_3(TMA)_2(H_2O)_3]_\infty$, where TMA is benzene-1,3,5-tricarboxylate) could be employed for detection in aqueous or humid media.

Figure 1:
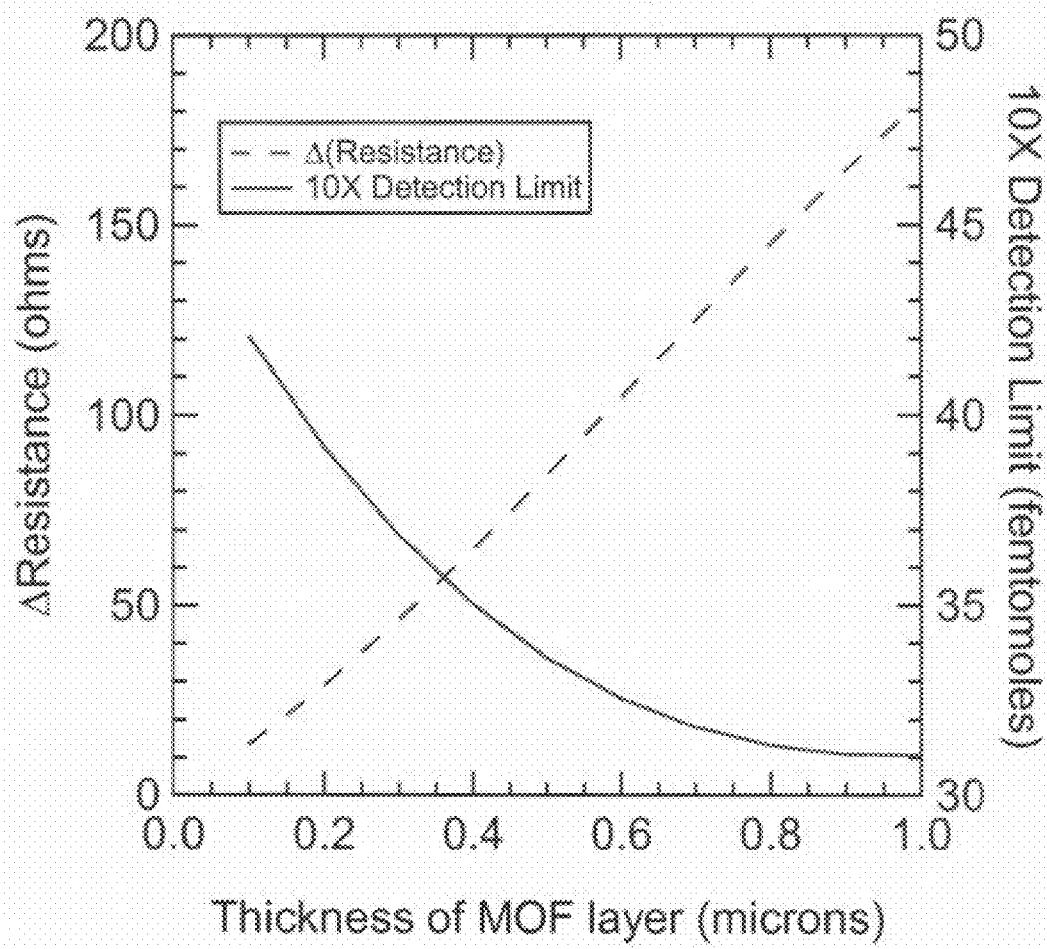
FIG. 1 shows the predicted resistance change and sensitivity of a microcantilever coated with IRMOF-1 as a function of the thickness of the CP surface layer.

We calculate the limit of sensitivity for CP-coated microcantilever using the equation for a bi-layer cantilever and IRMOF-1 (a well-characterized zinc-carboxylate CP) as an example. The volumetric expansion of this CP material will induce a deformation, such as stretching or a bending moment, in the microcantilever. This deformation can be related to tip deflection and stress in the piezoresistive part of the beam. Knowing the response function of the microcantilever and the elastic properties of the CP layer enables an estimate of the sensitivity of this device to be made. For an initial estimate we assume a cantilever having a length of 450 $\mu$m and a thickness of 1-$\mu$m comprised entirely of silicon dioxide (Young's Modulus E=170 GPa). Assuming a 1-$\mu$m thick IRMOF-1 layer with a Young's Modulus, E, of 2.4 GPa (measured by using a nano-indentation technique) will produce a deflection of ~1 nm/$\mu$m of strain. Here, the sensitivity of a Wheatstone bridge and galvanometer used to measure the resistance of the microcantilever assembly piezoresistor is calculated based upon atomic force microscopy (AFM) deflection tests to be about 1 m$\Omega$/nm of deflection. This corresponds to a resistance change of over 100 ohms for a CP film composed of IRMOF-1, which has a 0.8% linear strain (i.e., the unit cell dimension of this CP contracts about 0.8% after solvent adsorption). FIG. 1 shows the effect of varying the IRMOF-1 layer thickness on the measured resistance change. We can relate this to the absorption-induced deformation by calculating the total number of molecules adsorbed by the porous film. In this case the IRMOF-1 volume on the cantilever which can adsorb solvent molecules and change its unit cell dimensions is $1.8 \times 10^{-14}$ m$^3$. Hence, the limit of detection is based on the minimum detectable strain, which with our current instrumentation corresponds to a minimum detectable resistance change of about 0.005$\Omega$, corresponding to the absorption of about $8.5 \times 10^{-16}$ moles of DMF.

For IRMOF-1, X-ray crystal structures show that removal of the 8 DMF molecules contained in its pores following synthesis results in a 0.8% increase in the lattice constant. Although relatively small, the calculations described above predict this will induce a measurable stress in a microcantilever, assuming that effective mechanical bonding exists between the CP layer and the microcantilever. Again, assuming the dimensions of the microcantilever are 450 $\mu$m×40 $\mu$m×1 $\mu$m, we can calculate the resistance change, the cantilever tip deflection, and the number of molecules detected as a function of the MOF layer thickness. These calculated values of the resistance change induced by adsorption are shown graphically in FIG. 1. Also shown is an estimate of sensitivity of the measurements based on assuming a factor of 10 above the signal-to-noise (S/N) limit. The results clearly show that femtomole levels of adsorbates within a thin MOF layer can lead to easily measurable stresses, as shown by the magnitude of the predicted resistance. Therefore, this technique would provide an extremely sensitive detection mechanism.

Previous reports indicate that even absorption by weakly bonded spin-coated polymer layers leads to measurable stresses, but that methods that bind the coating tightly to the microcantilever are required to produce deflections approaching theoretical limits (cf. Singamaneni, S., McConney, M. E., LeMieux, M. C., Jiang, H., Enlow, J. O., Bunning, T. J., Naik, R. R., and Tsukruk, V. V., "Polymer-Silicon Flexible Structures for Fast Chemical Vapor Detection," *Advanced Materials*, 2007, v. 19: pp. 4248-4255; Goeders, K. M., Colton, J. S., and Bottomley, L. A., "Microcantilevers: Sensing Chemical Interactions via Mechanical Motion,"

*Chemical Reviews*, 2008, v. 108: pp. 522-542; and Battiston, E. M., Ramseyer, J.-P., Lang, H. P., Bailer, M. K., Gerber, Ch., Gimzcwski, J. K., Meyer, E., and Güntherodt, H.-J. "A chemical sensor based on a microfabricated cantilever array with simultaneous resonance-frequency and bending readout," *Sensors and Actuators 8*, 2001, v. 77: pp. 122 131). Therefore, using strong covalent bonds to attach CP layers to cantilever surfaces should transmit the induced stress very effectively. Furthermore, much larger changes in unit cell dimensions have been observed for CP materials other than IRMOF-1. For example, the copper MOF [$Cu_2$-$A_2B$] (where A=pyrazine-2,3-dicarboxylate; and B=4,4'-bipyridine) undergoes a 6.8% contraction along the b axis of the crystal when it adsorbs benzene (Matsuda, et al., "Guest shape-responsive fitting of porous coordination polymer with shrinkable framework," *Journal of the American Chemical Society.* 2004, v. 126(43): pp. 14063-14070). Thus, it may be possible to achieve even higher adsorbate sensitivities than predicted for IRMOF-1.

EXAMPLE

The following is an example of a fabrication method for coating microcantilever devices using a precipitative method for depositing carboxylate-based CP. It is illustrated here for the case of HKUST-1, a copper-carboxylate CP, but would be applicable to most CP in which the framework is constructed by coordinating the metal groups with carboxylate ligands. CP structures comprising metals coordinated to one or more types of electron donating groups such as, diazolates, tetrazolates, and the like, are also possible.

Figure 2A:
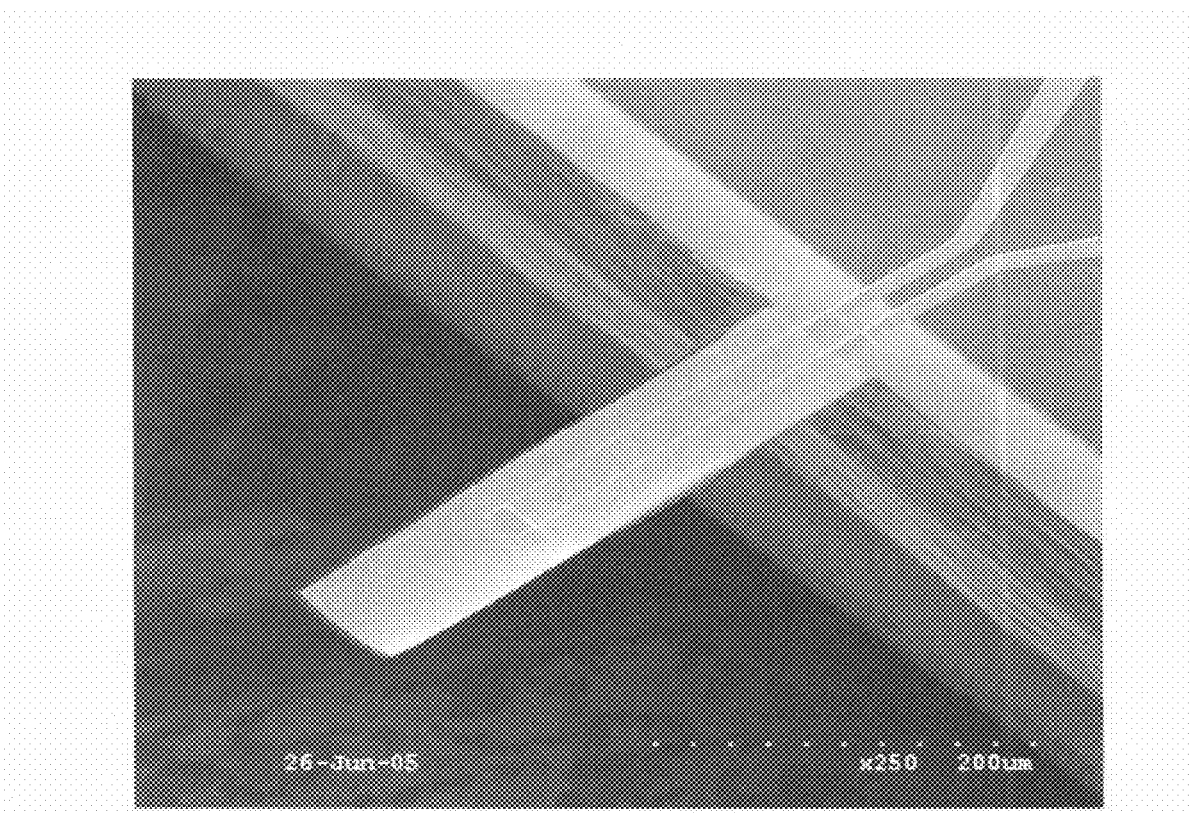
FIG. 2A shows a photomicrograph of an uncoated microcantilever device of an embodiment of the present invention.
Figure 2B:
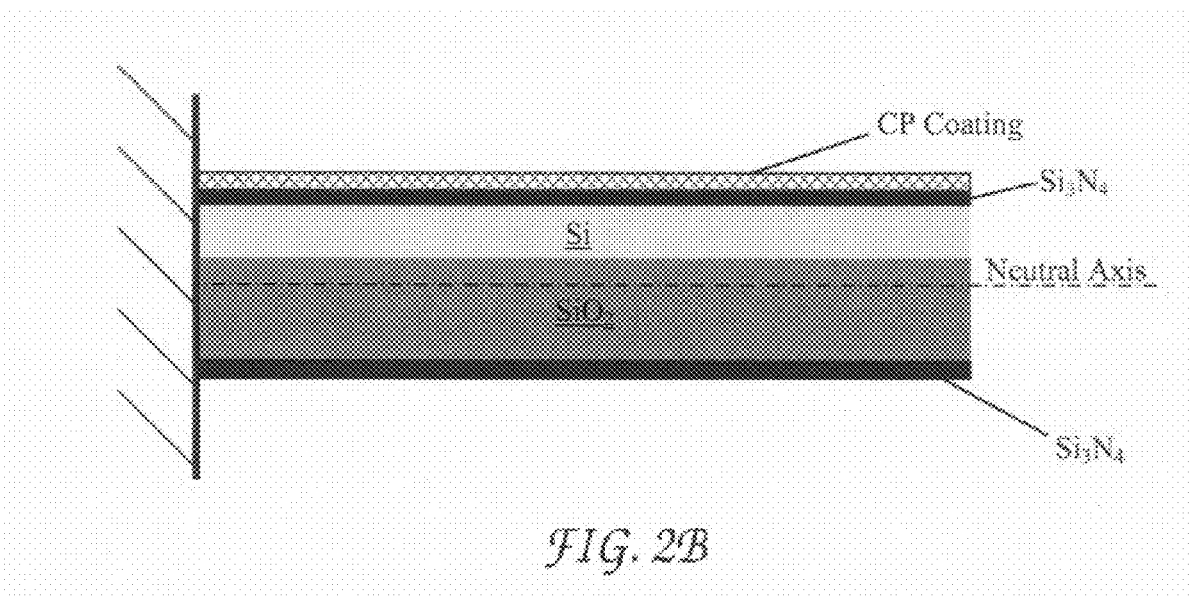
FIG. 2B shows a cross-sectional schematic representation of a CP-coated static microcantilever.

An example of the uncoated microcantilever device used herein is shown in FIG. 2A, while FIG. 2B shows a schematic of a cross-sectional view of the CP coated embodiment of the present invention. As presented herein, the device comprises a silicon dioxide microcantilever onto which is grown a thin layer of silicon on a top surface, and thin layers of silicon nitride on the top and bottom surfaces of the microcantilever, respectively. Furthermore, a thin layer of gold was evaporatively deposited onto the top surface of the microcantilever using a shadow mask to act as "seed" layer for the CP coating and prevent CP deposition on areas other than the microcantilever. Self-assembled monolayers (SAM) terminated with a carboxylic acid group were then grown on the surface using published procedures. The SAM-coated device was then submerged in solutions of the HKUST-1 precursors. For example, an array of SAM-coated microcantilevers (in this case eight on a chip) was sequentially immersed in a 1 mM solution of ($Cu(CH_3COO)_2 \cdot H_2O$) in ethanol for 30 minutes and then in a 1 mM of benzene-1,3,5-tricarboxylic acid (BTC) solution in ethanol for 1 hour at room temperature. Between each step the substrates were rinsed with ethanol.

Other attachment methods, of course, are also possible. These include, but should not be limited to, SAMs covalently bonded to any of alumina, silica, or other metal oxide coatings; coatings deposited by atomic layer deposition and terminated with a reactive group such as OH, halogen, $CO_2H$, amine and the like; SAMs deposited on metals other than gold; and SAMs terminated by electron-donating groups other than a carboxylic acid. Moreover, the CP coating may be grown directly onto any of the foregoing materials without the need for a SAM.

Not shown in FIG. 2B, is the piezoresistive sensor in order to avoid introducing undue complexity to the drawing.

Figure 2C:
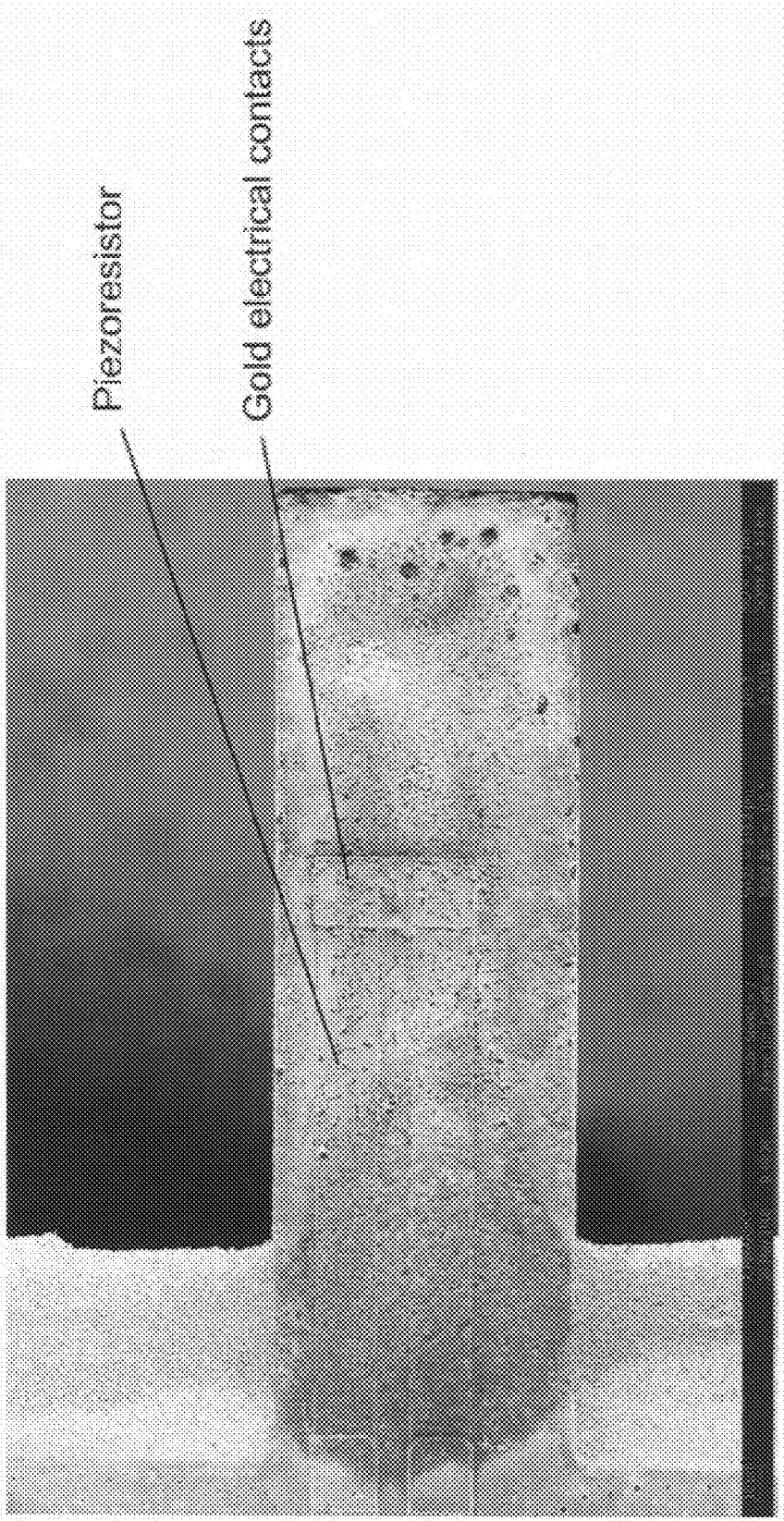
FIG. 2C shows a photomicrograph of a microcantilever device of an embodiment of the present invention coated with metal-organic framework HKUST-1.
Figure 2D:
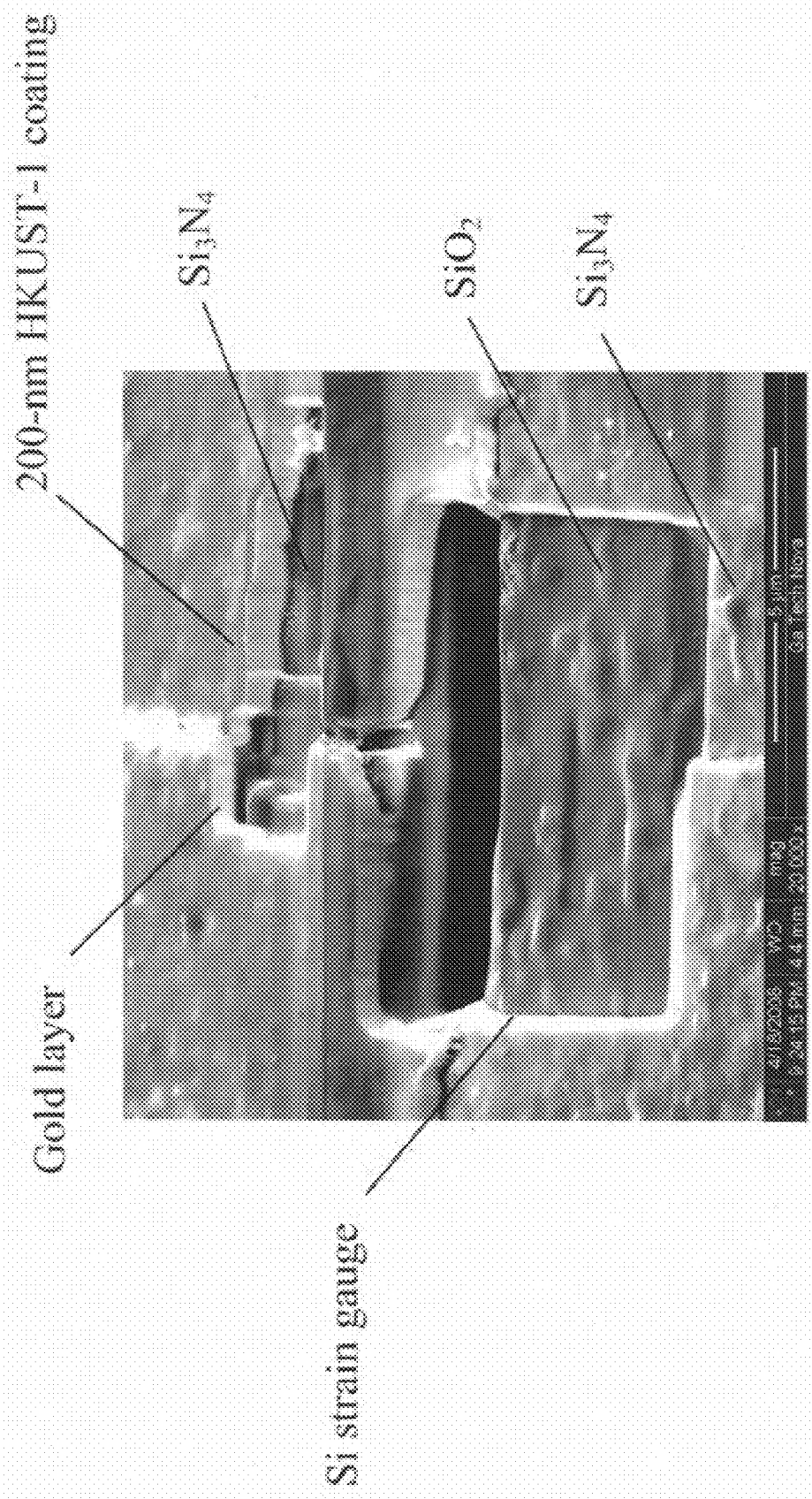
FIG. 2D shows details of the structure of a CP-coated microcantilever of an embodiment of the present invention similar to that shown in FIG. 2C, but revealing both the surface coating and the underlying device structure.

An example of the resulting coating is shown in FIGS. 2C and 2D. The coatings are somewhat rough but tightly adherent, as demonstrated by a scratch test performed on larger-scale substrates. Effective patterning is demonstrated by either the lack of HKUST-1 coating in areas of the device not pre-coated with gold or by weakly adherent coatings that are easily removed. Moreover, it is not necessary that the coating be continuous and in fact may be discontinuous and contain a plurality of "holes" across the coated surface. Additionally, the coating may be applied to one or both sides of the device depending on the sensitivity desired.

A low magnification SEM image of an entire microcantilever coated with the MOF HKUST-1 is shown in FIG. 2C. The coating is not perfect, being rather rough and somewhat non-uniform with respect to its microstructure. For example, larger "dots" to the right side of the image appear to be islands with a relatively smooth surface compared with the remainder of the film. The adsorption behavior, however, is completely consistent with published data providing confidence that minor irregularities in the coating do not substantially degrade the performance of the device (cf. Wang, Q. M., Shen, D., Billow, M., Lau, M. L., Deng, S., Fitch, F. R., Lemcoff, N. O., and Semanscin, J. "Metallo-organic molecular sieve for gas separation and purification," *Microporous and Mesoporous Materials*, 2002, v. 55: pp. 217-230).

Figure 3:
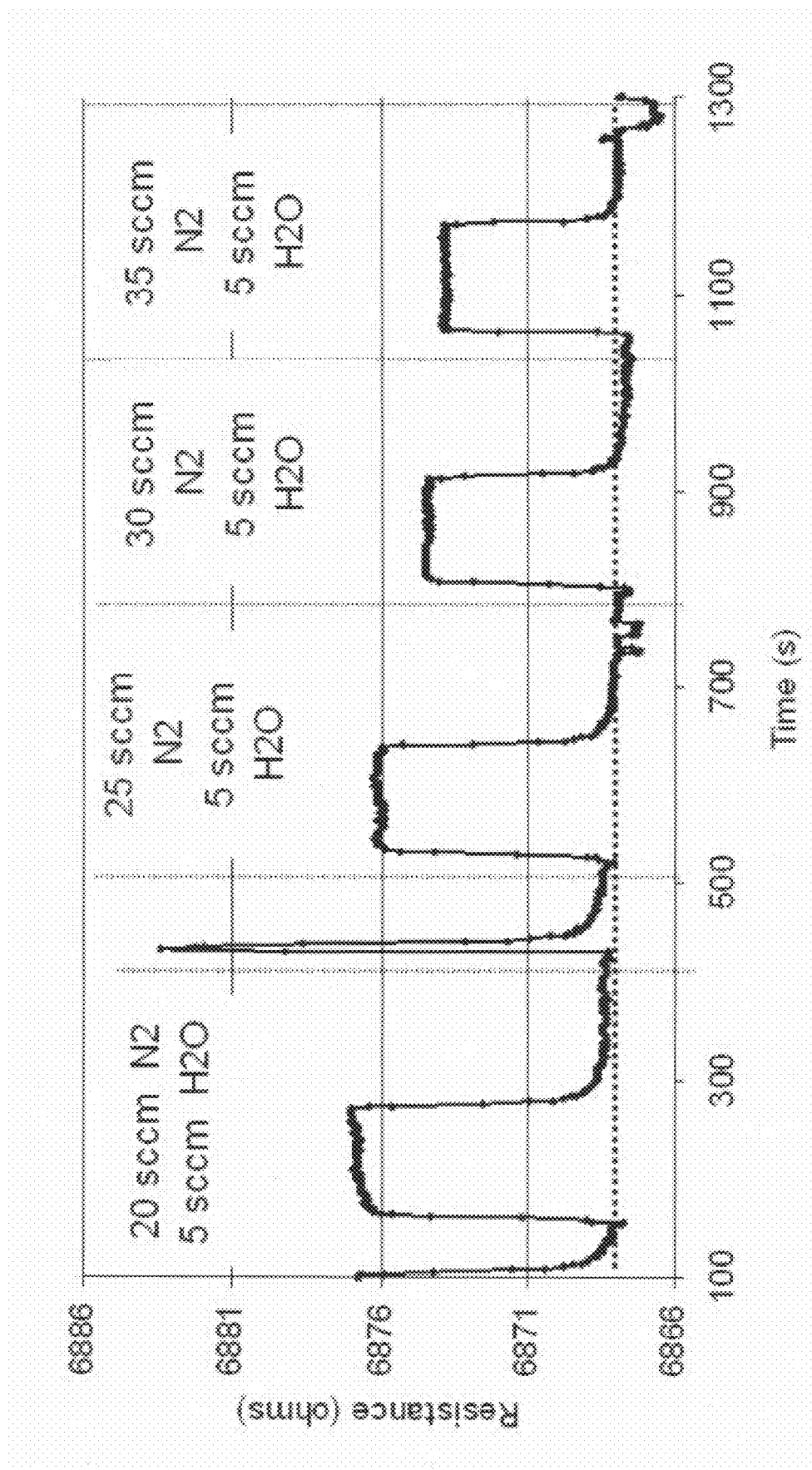
FIG. 3 shows the response of the CP-coated microcantilever of a preferred embodiment of the present invention to various water-vapor concentrations (the spike at 425 s is due to a pressure pulse in the system and is unrelated to the water measurement).

The sensor shown in FIG. 2C was presented with various concentrations of water vapor mixed with a stream of $N_2$ in order to measure its response to this gas mixture. An example of the sensor response is shown in FIG. 3 which plots the change in resistance of the sensor relative to an uncoated reference microcantilever as both are exposed to the stream nitrogen gas as a secondary stream of water vapor is started and then stopped several times over a period of about 20 minutes. The spike at ~425 s is a spurious pressure is pulse (an artifact) and is unrelated to the experiment.

Figure 4:
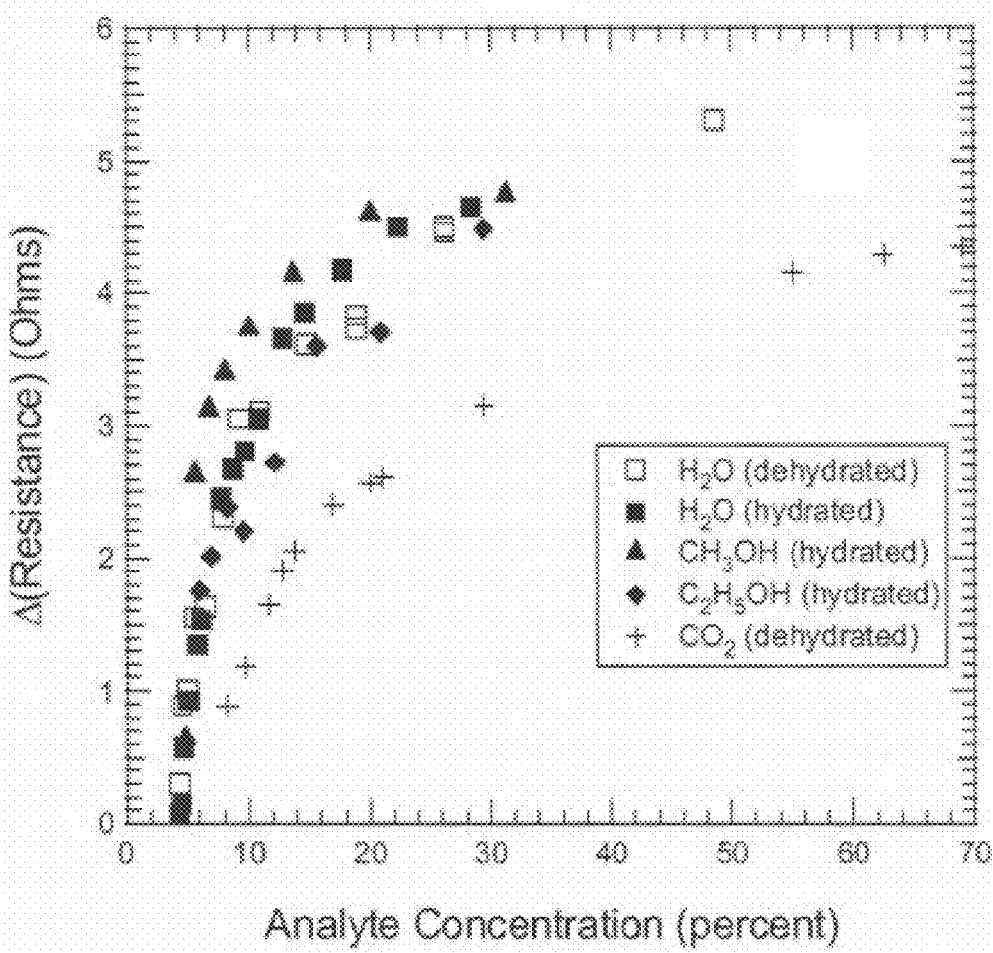
FIG. 4 summarizes the response of the CP-coated microcantilever of a preferred embodiment of the present invention to various gases.

Additional data is shown in FIG. 4. This figure shows the maximum resistance change observed for each target gas studied as a function of its concentration based on volume. The sensor was used in two configurations: the first having a CP layer containing two water molecules coordinated to the open axial coordination sites on MOF (i.e., hydrated); and the second having a CP layer that was dehydrated (50° C. for 2 hours) in order to remove coordinated water molecules, as well as any other physisorbed water that was or might be present. In the latter case, we see a response to $CO_2$ that is not observed when the CP layer was in the hydrated state.

Also noted: 1) the response of the sensor to $H_2O$ is essentially the same whether the CP coating is hydrated or dehydrated (the same is true of methanol, although the dehydrated data are not shown for the sake of clarity); 2) The response of the sensor to ethanol is significantly different from its response to methanol, suggesting that these species could be distinguished from one another through a judicious choice of CP layer; and 3) Only the $CO_2$ data for the dehydrated sensor are shown since there is no response when the CP layer is hydrated.

Lastly, the piezoresistive element further includes a low voltage power supply which may be used to heat the microcantilever and CP coating by resistance heating. This provides the user with the ability to desorb the CP coating of the absorbed chemical analyte thereby allowing for a multiplicity of measurements with the same device.

Having thus described exemplary embodiments of the present invention, it should be noted by those skilled in the art that the disclosures herein are exemplary only and that various other alternatives, adaptations, and modifications may be made within the scope of the present invention. Accordingly, the present invention is not to be construed as limited to only the specific embodiment illustrated herein.

Finally, to the extent necessary to understand or complete the disclosure of the present invention, all publications, patents, and patent applications mentioned herein are expressly incorporated by reference therein to the same extent as though each were individually so incorporated.

We claim:

1. A sensing device for detecting the presence of a chemical analyte, comprising:
   a microcantilever structure comprising top and bottom surfaces and a cantilever length; and
   a continuous or discontinuous absorbent crystalline layer attached to one or both of the top and bottom surfaces along at least a portion of the cantilever length, wherein the absorbent crystalline layer comprises a coordination polymer (CP) coating having a crystal lattice, wherein the crystal lattice dimensions change as the layer absorbs the chemical analyte, causing strain in the microcantilever structure, thereby signaling the presence of the chemical analyte.

2. The sensing device of claim 1, wherein the CP coating comprises a metal organic framework.

3. The sensing device of claim 1, wherein the CP coating comprises a zeolite imidazolate framework.

4. The sensing device of claim 1, wherein the CP coating comprises any crystalline material comprised of organic and/or inorganic portions and consisting of a porous structure.

5. The sensing device of claim 1, further comprising a metal or metal oxide layer attached to one or both of the top and bottom surfaces, wherein the CP coating is attached to the metal or metal oxide layer.

6. The sensing device of claim 5, further comprising a self-assembled monolayer (SAM) attached to the metal or metal oxide layer, wherein the CP coating is attached to the SAM.

7. The sensing device of claim 6, wherein the CP coating is grown from one or more reactant solutions onto the SAM.

8. The sensing device of claim 7, wherein the reactant solutions comprise benzene-1,3,5-tricarboxylic acid and copper acetate dissolved in a quantity of ethanol.

9. The sensing device of claim 7, wherein the reactant solutions comprise benzene-2-R',4-R'',6-R'''-1,3,5-tricarboxylic acid and R', R'', and R''' can be H, X (where X is halogen), alkyl, OH, $NO_2$, $NH_2$, OR (where R is an alkyl group) or any other chemical atom or group attached at these positions, and copper acetate dissolved in a quantity of ethanol.

10. The sensing device of claim 5, wherein the metal layer is formed by a process selected from the list of processes consisting of chemical vapor deposition, physical vapor deposition, and electrolytic deposition.

11. The sensing device of claim 5, wherein the metal oxide layer is formed by an atomic layer deposition process.

12. The sensing device of claim 1, further comprising a reference sensing device for providing a baseline reference, wherein the reference sensing device comprises a microcantilever structure without a CP layer.

13. The sensing device of claim 1, further comprising a plurality of sensing devices.

14. The sensing device of claim 1, wherein the sensing device senses molecular species selected from the list consisting of water vapor, carbon dioxide, methanol, ethanol, carbon monoxide, nitric oxide, nitrous oxide, organic amines, and organic compounds containing $NO_2$ groups.

15. The sensing device of claim 1, in which the response of the sensor is controlled by the hydration state of the CP layer.

16. A sensing device for detecting the presence of a chemical analyte, comprising:
   a microcantilever structure comprising top and bottom surfaces and a cantilever length; and
   a continuous or discontinuous absorbent crystalline layer attached to one or both of the top and bottom surfaces along at least a portion of the cantilever length, wherein the absorbent crystalline layer comprises a covalent organic framework having a crystal lattice, wherein the crystal lattice dimensions change as the layer absorbs the chemical analyte, causing strain in the microcantilever structure, thereby signaling the presence of the chemical analyte.

17. A method for detecting the presence of a chemical species, comprising the steps of:
   providing a microcantilever structure comprising a piezoresistive element fixedly attached to a first surface of the microcantilever structure, wherein the piezoresistive element electrically communicates with a resistance sensing meter;
   applying a continuous or discontinuous thickness of a coordination polymer (CP) coating comprising a porous crystalline structure and having a crystal lattice onto the first surface of a microcantilever structure covering at least a major portion of the first surface and the piezoresistive element; and
   exposing the coated microcantilever structure to an environment containing the chemical species, wherein the crystal lattice changes dimension as the CP coating absorbs the chemical species, thereby causing strain in the microcantilever structure and causing a subsequent change in the resistance of the piezoresistive element, thereby signaling the presence of the chemical species.

18. The method of claim 17, wherein the CP coating comprises a metal organic framework.

19. The method of claim 17, wherein the CP coating comprises a zeolite imidazolate framework.

20. The method of claim 17, wherein the CP coating comprises any crystalline material comprised of organic and/or inorganic portions and consisting of a porous structure.

21. The method of claim 17, wherein the step of applying further comprises applying a metal or metal oxide layer to one or both of the top and bottom surfaces followed by applying the CP layer.

22. The method of claim 21, further comprising a self-assembled monolayer (SAM) attached to the metal or metal oxide layer.

23. The method of claim 22, wherein the CP coating is grown from one or more reactant solutions onto the SAM.

24. A method for detecting the presence of a chemical species, comprising the steps of:
   providing a microcantilever structure comprising a piezoresistive element fixedly attached to a first surface of the microcantilever structure, wherein the piezoresistive element electrically communicates with a resistance sensing meter;
   applying a continuous or discontinuous thickness of a covalent organic framework comprising a porous crystalline structure and having a crystal lattice onto the first surface of a microcantilever structure covering at least a major portion of the first surface and the piezoresistive element; and
   exposing the coated microcantilever structure to an environment containing the chemical species, wherein the crystal lattice changes dimension as the covalent organic framework absorbs the chemical species, thereby causing strain in the microcantilever structure and causing a subsequent change in the resistance of the piezoresistive element, thereby signaling the presence of the chemical species.

* * * * *